United States Patent
Portnoy et al.

[11] Patent Number: 6,089,232
[45] Date of Patent: Jul. 18, 2000

[54] SNORE STOPPER

[76] Inventors: Leonard L. Portnoy, 8950 Olympic Blvd.; Alex A. Farnoosh, 8920 Wilshire Blvd. #517, both of Beverly Hills, Calif. 90211

[21] Appl. No.: 09/310,526

[22] Filed: May 12, 1999

Related U.S. Application Data

[63] Continuation-in-part of application No. 09/195,285, Nov. 18, 1998, abandoned.

[51] Int. Cl.⁷ ...................................................... A61F 5/56

[52] U.S. Cl. ........................... 128/848; 128/859; 602/902

[58] Field of Search ................................. 128/846, 848, 128/859–862; 602/902

[56] References Cited

U.S. PATENT DOCUMENTS

| | | | |
|---|---|---|---|
| 1,354,652 | 10/1920 | Jefferies | 128/848 |
| 2,574,623 | 11/1951 | Clyde | 128/848 |
| 4,711,237 | 12/1987 | Kaiser | 128/859 |
| 4,883,072 | 11/1989 | Bessler | 128/857 |

*Primary Examiner*—Michael A. Brown
*Attorney, Agent, or Firm*—Sanford Astor

[57] ABSTRACT

A method and device for stopping a person from snoring while sleeping including an elastic fabric panel, having adhesive covering one surface, the adhesive covered by a protective peel-off cover sheet. A narrow slit is cut through the panel near the center of the panel. The panel is adapted to fit tightly over the mouth and lips of the person, held by the adhesive to the face, preventing the mouth from opening while sleeping, which prevents snoring, but enables mouth breathing and talking.

12 Claims, 1 Drawing Sheet

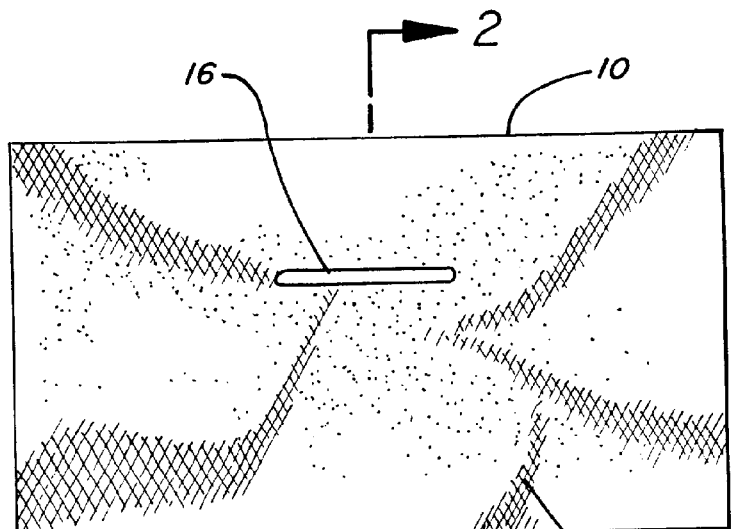
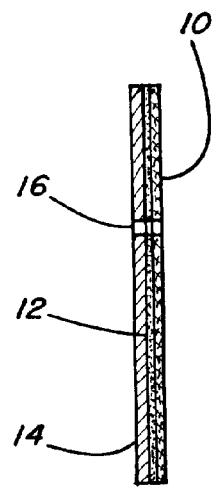
FIG. 1    FIG. 2
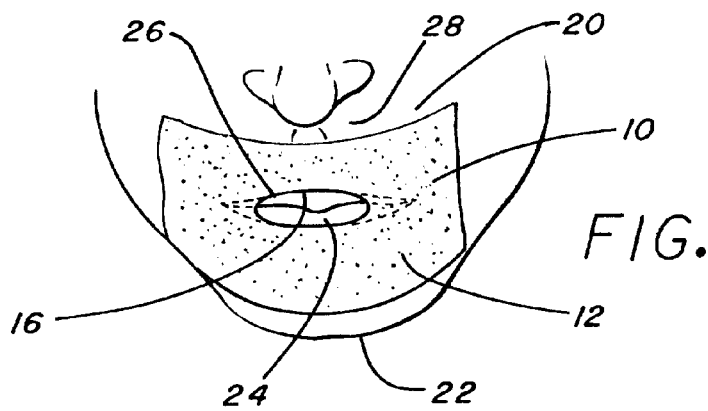
FIG. 3
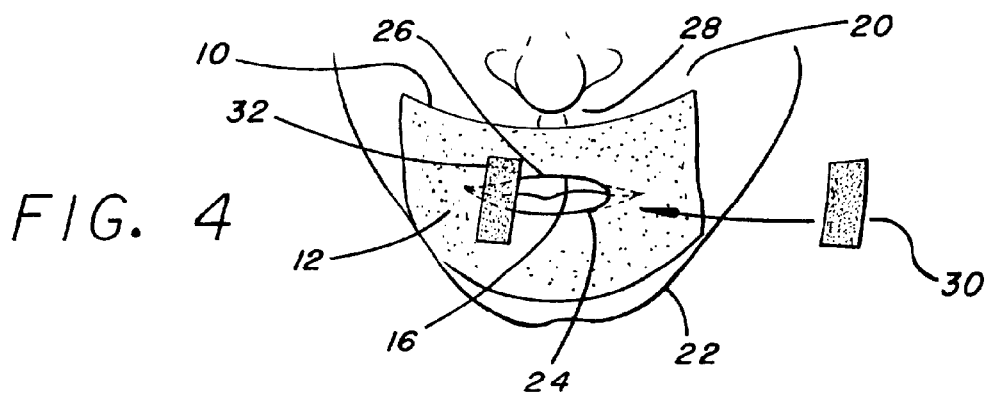
FIG. 4

SNORE STOPPER

This application is a continuation-in-part of our co-pending application, Ser. No. 09/195,285 filed Nov. 18, 1998, now abondoned.

BACKGROUND OF THE INVENTION

It has been estimated that ninety million American adults and children snore and that one in every ten adults snores. Although snoring has no serious medical consequences for most people, for an estimated one in one hundred snorers, habitual snoring is the first indication of a potentially life-threatening sleep disorder called Obstructive Sleep Apnea. If not diagnosed or if left untreated, Obstructive Sleep Apnea could result in severe medical consequences such as systemic high blood pressure, cardiovascular disease and even sudden death.

Many people think that snoring and apnea are the same thing. This is not true. Snoring, which is caused by vibration of the tissues due to air turbulence as the airway narrows, may be a sign that a patient is suffering from apnea. But not all snorers suffer from apnea.

Snoring can be categorized by its severity. At one end of the scale is the benign snorer who snores but experiences no physical problems. On the other end is the snorer who suffers from apnea, and in the middle is the snorer who suffers from upper airway resistance syndrome. In these people, though they may not actually experience apneic episodes, their snoring is so loud and their breathing so labored, that it still wakes them, and their partners, numerous times throughout the night Millions of spouses, partners and/or children suffer through the night by the annoying noise of the snorer. Snoring not only disturbs the sleeping pattern of the snorer himself, it is also disruptive to the family life by causing lack of sleep to all involved. This leaves all involved unrefreshed, tired and sleepy throughout the day. It can cause sleepiness while driving, reading, working or doing other tasks.

Snoring generally comes from opening the mouth while sleeping. A broad variety of intra-oral and dental appliances and devices are now available to treat a patient for snoring. The known oral devices for treating snoring and obstructive sleep are worn inside of the mouth and work by repositioning of the jaw, moving the mandible, lifting the soft palate or moving the tongue forward. The various classes of treatment devices that now exist include mandibular advancers and tongue advancers. These appliances work by advancing the tongue and soft palate away from the back wall of the throat. The tongue advancers are used when the jaw joints do not tolerate stretching or when there are insufficient teeth to support a mandibular advancer. Other methods used to treat snoring include controlled positive air flow pressure systems also known as CPAP which require a nose mask and which are quite uncomfortable. The function of the CPAP treatment is enhanced using Applicant's invention.

All of these known devices suffer from having to be worn inside of the mouth, they are uncomfortable to wear and they are expensive and must be fitted and made to order. These devices also often cause excessive salivation, dry mouth or tempomandibular joint (TMJ) discomfort.

Other treatments for snoring include various surgeries, which are drastic steps to take to attempt to cure the problem, however snoring can be so disruptive to a person's life and relationships, that some sufferers resort to surgery.

Another device which has been known is that described in U.S. Pat. Nos. 5,640,974 and 5,690,121 to Miller. Miller's device comprises a flexible sheet with adhesive, cut in a U-shape. It attempts to keep the mouth closed by covering only the "remote end" of the lips. It is highly ineffective because the two "cheek attachment" strips come loose very easily with any movement of the mouth and the entire device falls off, and because the limited covering of the mouth and lips is ineffective to keep the mouth closed. In addition, the loose ends make it difficult to apply and the backing of the tape difficult to peel off.

OBJECTS OF THE INVENTION

Accordingly, several objects and advantages of the invention are as follows:

It is an object of this invention to provide a simple device to prevent snoring.

It is another object of this invention to provide an externally worn device to prevent snoring.

Further objects and advantages will become apparent from a consideration of the following description and drawings.

BRIEF DESCRIPTION OF THE DRAWINGS

FIG. 1 is a front view of the snore stopper device of this invention;

FIG. 2 is a front view of a person wearing the device; and

FIG. 3 is a front view of a person wearing the device.

FIG. 4 is a front view of a person wearing an alternate embodiment of the device.

DETAILED DESCRIPTION OF THE INVENTION

Referring now to the drawings, there is shown a panel 10 having an adhesive layer or backing 12 and a peel-off, protective cover sheet 14 which covers adhesive backing 12. A narrow horizontal slit 16 is cut through panel 10, near its center. After the peel-off protective layer 14 is removed, the adhesive side 12 of panel 10 is applied over the mouth and lips, so that it is difficult but possible for the user 20 to open his or her mouth minimally. This has proved to prevent snoring.

Panel 10 is made from an elastic fabric or material having an adhesive backing, such as "Hypafix" manufactured by, and a trademark of, Smith & Nephew, and sold as a dressing retention sheet. A similar product is manufactured by Beirsdorf, Inc. under the trademark "Cover-Roll" stretch. Both of these materials are cross-elastic, that is, elastic in all directions, which greatly aids in the effectiveness of the snore stopper of this invention. These products are also hypo-allergenic and self-adhesive.

For best results the narrow slit 16 is cut slightly above center, about ¼ to ½ inch above the center line of panel 10. The slit is made about ½ inch to 1¼ inches long. The slit is required for proper breathing, speaking and safety.

Panel 10 is applied to the face of the user, usually just before going to bed for the night. For best results, the user must protrude his or her chin 22 forward and push his or her lower lip 24 forward and upward over the entire upper lip 26. Panel 10, after removal of peel-off layer 14, is then applied by affixing adhesive layer 12 to the chin 22 and the tissue surrounding the chin, and then while pulling in an upward direction, stretching and affixing panel 10 over the lower lip 24 and mouth and over the sides of the lips and then over upper lip 26 and the skin tissue 28 above upper lip 26. The sides of the lips, about one-third of the lips on each side, are covered by panel 10, which leaves about one-third of the mouth and lips uncovered at slit 16, but the mouth is effectively held closed by panel 10. This method effectively prevents snoring.

Referring to FIG. 3, in the event panel 10 fails to sufficiently cover the outside edges of the lips, about one-third on each side, cover strips 30 and 32 may be affixed to the face of panel 10 to make sure that enough of the edges of the lips are sufficiently covered. Cover strips 30 and 32 are made of the same material as panel 10 and are affixed over panel 10 by their self-adhesive layer 12 after removal of protective layer 14. Strips 30 and 32 can be cut from an extra panel 10 by the wearer when needed. Strips 30 and 32 are only large enough to cover the area desired and adhere to the face of panel 10. They never extend past the edges of panel 10.

The material of panel 10 stretches in all directions as it is applied, while pulling in an upward direction, to pull lower lip 24 over upper lip 26, and as a result of the elasticity of panel 10, slit 16 is expanded into a wider, round or oval opening at the level of the mouth. By cutting the slit 16 just above the center line of panel 10, slit 16 will end up, after panel 10 is stretched and affixed, directly opposite the opening of the mouth, where the lower lip 24 and upper lip 26 meet.

When panel 10 is applied in this manner, the user can both breath and talk, but cannot open his or her mouth more than a very small opening, which allows breathing but effectively prevents snoring. The elasticity of the fabric aids in keeping the mouth closed and thus aids the effectiveness of the device. When applied as set forth above, the bias of the elasticity of the fabric acts to try to return the fabric to its unstretched condition, causing a force in the direction of closing the mouth.

While sleeping or resting the mouth is held in a comfortable position. In order to speak, the user, with a small effort, can slightly open the mouth due to the elastic quality of the fabric or material, but after speaking and closing the mouth, the elastic fabric substantially returns substantially to its initial state and the mouth to a relaxed position, comfortably closed.

Panel 10 can be of any convenient size so long as it is big enough to fit over a portion of the chin and the tissue surrounding the mouth and lips. The protective peel-off layer 14 may have a cut across it which makes it easier to remove. Panel 10 is disposable and is discarded after each use and a new one is applied each night.

The device described is quite effective in preventing snoring by keeping the mouth closed while sleeping. It is worn extra-orally and so is much easier to tolerate than the intra-oral devices now available. This invention has been tested on individuals with snoring problems and it has prevented snoring while sleeping. Furthermore, the persons tested have experienced little or no discomfort. The device of this invention is the easiest, least expensive, yet most effective treatment for severe snoring problems yet devised.

Having thus described the invention, it is requested that the invention be described by the scope of the following claims.

We claim:

1. A method for preventing a person from snoring while sleeping comprising affixing an elastic panel having an adhesive backing and a narrow horizontal slit cut therein, over the mouth and upper and lower lips of the person, tightly enough to prevent the person's mouth from opening during sleep.

2. The method of claim 1 in which the panel is applied by the person protruding the chin forward and then the lower lip forward and upward over the upper lip, affixing the adhesive backing to the chin and then, while pulling the panel in an upward direction, stretching the panel and affixing the adhesive backing over the lower lip and then over the mouth, upper lip and the tissue above the upper lip.

3. The method of claim 2 in which the panel is affixed so as to cover the outer one-third of the lips on both sides of the lips leaving the center one-third of the lips uncovered.

4. The method of claim 3 comprising adhering a pair of separate strips to the face of the panel, each strip further covering portions of the lips.

5. A device for preventing a person from snoring through his or her mouth while sleeping comprising an elastic panel adapted to fit over the mouth and lips of the person, an adhesive backing covering one side of said panel adapted to affix the panel over the mouth and lips of the person to hold the person's mouth closed while sleeping, a narrow horizonatal slit cut in the panel adjacent the person's mouth to provide an opening at the mouth.

6. The device of claim 5 further comprising a peel-off protective layer over the adhesive backing.

7. The device of claim 6 in which the protective layer has a cut across its surface to aid in removing it from the adhesive backing.

8. The device of claim 5 in which the narrow slit is located just above the center line of the panel.

9. The device of claim 8 in which the slit is about one-quarter inch to one and one-quarter inches long and is cut about one-quarter to one-half inch above the center line of the panel.

10. The device of claim 5 in which the panel is cross-elastic.

11. The device of claim 5 in which the panel is hypoallergenic.

12. The device of claim 5 further comprising a pair of adhesive strips adapted to be affixed to the face of the panel to further cover portions of the lips and make the opening at the mouth smaller.

* * * * *